United States Patent
Størup

(10) Patent No.: US 11,202,716 B2
(45) Date of Patent: Dec. 21, 2021

(54) HEAT AND SWEAT MANAGEMENT SYSTEM

(71) Applicant: Ossur Iceland ehf, Reykjavik (IS)

(72) Inventor: Martin Lund Størup, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 22 days.

(21) Appl. No.: 16/160,445

(22) Filed: Oct. 15, 2018

(65) Prior Publication Data

US 2019/0117420 A1 Apr. 25, 2019

Related U.S. Application Data

(60) Provisional application No. 62/574,852, filed on Oct. 20, 2017.

(51) Int. Cl.
*A61F 2/80* (2006.01)
*A61F 2/78* (2006.01)
(Continued)

(52) U.S. Cl.
CPC .............. *A61F 2/80* (2013.01); *A61F 2/68* (2013.01); *A61F 2/76* (2013.01); *A61F 2/7812* (2013.01);
(Continued)

(58) Field of Classification Search
CPC .... A61F 2/80; A61F 2/7812; A61F 2002/802; A61F 2002/807
See application file for complete search history.

(56) References Cited

U.S. PATENT DOCUMENTS

| | | |
|---|---|---|
| 708,685 A | 9/1902 | White |
| 4,655,779 A | 4/1987 | Janowiak |

(Continued)

FOREIGN PATENT DOCUMENTS

| | | |
|---|---|---|
| CN | 202051853 U | 11/2011 |
| CN | 105422926 A | 3/2016 |

(Continued)

OTHER PUBLICATIONS

Bertels et al., "Breathable Liner for Transradial Prostheses," Proceedings of the 2011 MyoElectric Controls/Powered Prosthetics Symposium, Aug. 14, 2011, 3 Pages.

(Continued)

*Primary Examiner* — Bruce E Snow
(74) *Attorney, Agent, or Firm* — Workman Nydegger

(57) ABSTRACT

A prosthetic system includes a prosthetic liner adapted to provide an interface between a residual limb and a prosthetic socket, and a valve assembly. The valve assembly is arranged for regulating fluid communication between an interface region defined between the prosthetic liner and the residual limb and a suspension chamber defined between the prosthetic liner and the prosthetic socket. A vacuum in the suspension chamber selectively moves the valve assembly between a closed position in which the valve assembly fluidly separates the suspension chamber from the interface region, and an open position in which a portion of the vacuum in the suspension chamber draws fluid from the interface region via the valve assembly into the suspension chamber.

7 Claims, 5 Drawing Sheets

(51) Int. Cl.
- *A61F 2/68* (2006.01)
- *A61F 2/76* (2006.01)
- *A61F 2/74* (2006.01)
- *A61F 7/00* (2006.01)

(52) U.S. Cl.
CPC .......... *A61F 2/74* (2021.08); *A61F 2002/766* (2013.01); *A61F 2002/7655* (2013.01); *A61F 2002/7665* (2013.01); *A61F 2002/802* (2013.01); *A61F 2002/805* (2013.01); *A61F 2002/807* (2013.01); *A61F 2007/0051* (2013.01)

(56) References Cited

U.S. PATENT DOCUMENTS

| | | |
|---|---|---|
| 4,869,250 A | 9/1989 | Bitterly |
| 4,977,927 A | 12/1990 | Hill |
| 5,258,037 A | 11/1993 | Caspers |
| 5,480,455 A | 1/1996 | Norvell |
| 5,534,034 A | 7/1996 | Caspers |
| 5,571,208 A | 11/1996 | Caspers |
| 5,885,509 A | 3/1999 | Kristinsson |
| 6,010,528 A | 1/2000 | Augustine et al. |
| 6,136,039 A | 10/2000 | Kristinsson et al. |
| 6,485,776 B2 | 11/2002 | Janusson et al. |
| 6,626,852 B2 | 9/2003 | Janusson et al. |
| 6,706,364 B2 | 3/2004 | Janusson et al. |
| 6,923,834 B2 | 8/2005 | Karason |
| 6,974,484 B2 | 12/2005 | Caspers |
| 7,001,563 B2 | 2/2006 | Janusson et al. |
| 7,105,122 B2 | 9/2006 | Karason |
| 7,118,602 B2 | 10/2006 | Bjarnason |
| 7,488,349 B2 | 2/2009 | Einarsson |
| 7,771,487 B2 | 8/2010 | Mantelmacher |
| 7,867,286 B2 | 1/2011 | Einarsson |
| 7,922,775 B2 | 4/2011 | Caspers |
| 8,034,120 B2 | 10/2011 | Egilsson et al. |
| 8,052,760 B2 | 11/2011 | Egilsson et al. |
| 8,097,043 B2 | 1/2012 | Egilsson |
| 8,114,167 B2 | 2/2012 | Caspers |
| 8,182,547 B2 | 5/2012 | King |
| 8,308,815 B2 | 11/2012 | Mccarthy |
| 8,308,817 B2 | 11/2012 | Egilsson et al. |
| 8,372,159 B2 | 2/2013 | Mackenzie |
| 8,382,852 B2 | 2/2013 | Laghi |
| 8,394,150 B2 | 3/2013 | Laghi |
| 8,444,703 B2 | 5/2013 | Slemker et al. |
| 8,475,537 B2 | 7/2013 | King |
| 8,480,759 B2 | 7/2013 | Pacanowsky et al. |
| 8,535,389 B2 | 9/2013 | Mckinney |
| 8,679,194 B2 | 3/2014 | Mackenzie |
| 8,808,394 B2 | 8/2014 | Laghi |
| 8,894,719 B2 | 11/2014 | Egilsson et al. |
| 8,911,506 B2 | 12/2014 | Egilsson et al. |
| 8,956,422 B2 | 2/2015 | Halldorsson |
| 8,978,224 B2 | 3/2015 | Hurley et al. |
| 9,044,348 B2 | 6/2015 | Halldorsson et al. |
| 9,050,201 B2 | 6/2015 | Egilsson et al. |
| 9,056,022 B2 | 6/2015 | Egilsson et al. |
| 9,060,885 B2 | 6/2015 | Egilsson et al. |
| 9,066,821 B2 | 6/2015 | Egilsson et al. |
| 9,072,611 B2 | 7/2015 | Mackenzie |
| 9,072,617 B2 | 7/2015 | Halldorsson et al. |
| 9,155,636 B1 | 10/2015 | Fikes |
| 9,168,157 B2 | 10/2015 | Mackenzie |
| 9,180,027 B2 | 11/2015 | Kettwig et al. |
| 9,198,780 B2 | 12/2015 | Jonsson et al. |
| 9,295,567 B2 | 3/2016 | Egilsson et al. |
| 9,398,963 B2 | 7/2016 | King |
| 9,468,542 B2 | 10/2016 | Hurley et al. |
| 9,486,335 B2 | 11/2016 | Halldorsson et al. |
| 9,615,946 B2 | 4/2017 | Halldorsson et al. |
| 9,629,732 B2 | 4/2017 | Egilsson et al. |
| 2001/0016781 A1 | 8/2001 | Caspers |
| 2003/0109908 A1 | 6/2003 | Lachenbruch et al. |
| 2004/0122528 A1 | 6/2004 | Egilsson |
| 2005/0149202 A1 | 7/2005 | Schaffer et al. |
| 2007/0055383 A1* | 3/2007 | King ............... A61F 2/68 623/34 |
| 2007/0162153 A1 | 7/2007 | Barnes et al. |
| 2007/0213839 A1 | 9/2007 | Nachbar |
| 2008/0046078 A1 | 2/2008 | Singer |
| 2008/0221705 A1 | 9/2008 | Scussel |
| 2010/0125342 A1 | 5/2010 | King |
| 2010/0185300 A1 | 7/2010 | Mackenzie |
| 2010/0256780 A1 | 10/2010 | So |
| 2010/0274364 A1 | 10/2010 | Pacanowsky et al. |
| 2010/0312360 A1 | 12/2010 | Caspers |
| 2011/0071649 A1 | 3/2011 | Mckinney |
| 2011/0092935 A1 | 4/2011 | Hann |
| 2011/0144769 A1 | 6/2011 | Nakamura |
| 2011/0282466 A1* | 11/2011 | Laghi ............... A61F 2/7812 623/36 |
| 2012/0109336 A1* | 5/2012 | Laghi ............... A61F 2/7812 623/33 |
| 2012/0191217 A1 | 7/2012 | Mackenzie |
| 2013/0025315 A1 | 1/2013 | Freeman et al. |
| 2013/0053982 A1 | 2/2013 | Halldorsson |
| 2013/0103125 A1 | 4/2013 | Radspieler et al. |
| 2014/0025183 A1 | 1/2014 | Kelley et al. |
| 2014/0249650 A1 | 9/2014 | Laghi et al. |
| 2014/0277584 A1 | 9/2014 | Hurley et al. |
| 2014/0277585 A1 | 9/2014 | Kelley et al. |
| 2014/0289924 A1 | 10/2014 | Cleveland |
| 2014/0379097 A1 | 12/2014 | Hurley et al. |
| 2015/0079014 A1 | 3/2015 | Ingvarsson et al. |
| 2015/0238330 A1 | 8/2015 | Jonsson |
| 2015/0359644 A1 | 12/2015 | Sanders et al. |
| 2016/0022442 A1 | 1/2016 | Kettwig et al. |
| 2016/0030206 A1 | 2/2016 | Abu Osman et al. |
| 2016/0081822 A1 | 3/2016 | Zhe et al. |
| 2016/0143752 A1 | 5/2016 | Hurley et al. |
| 2016/0199202 A1 | 7/2016 | Jonasson et al. |
| 2016/0338858 A1 | 11/2016 | Hurley et al. |
| 2016/0338859 A1 | 11/2016 | Sverrisson et al. |
| 2016/0346100 A1 | 12/2016 | Sverrisson et al. |
| 2017/0027719 A1 | 2/2017 | Bache et al. |
| 2017/0027720 A1 | 2/2017 | Pedtke et al. |
| 2017/0056212 A1 | 3/2017 | Jonsson et al. |
| 2017/0105853 A1 | 4/2017 | Jonsson et al. |
| 2017/0128238 A1 | 5/2017 | Hurley et al. |
| 2017/0216057 A1 | 8/2017 | Egilsson et al. |
| 2017/0333223 A1 | 11/2017 | Rasmussen et al. |
| 2018/0000615 A1 | 1/2018 | Hurley et al. |
| 2018/0021153 A1 | 1/2018 | Hurley et al. |
| 2018/0036151 A1 | 2/2018 | Garus et al. |

FOREIGN PATENT DOCUMENTS

| | | |
|---|---|---|
| DE | 102010020262 A1 | 11/2011 |
| EP | 0363654 A2 | 4/1990 |
| EP | 1875881 A1 | 1/2008 |
| EP | 2178481 B1 | 11/2016 |
| EP | 3150120 B1 | 10/2018 |
| JP | 2015058013 A | 3/2015 |
| SU | 829095 A1 | 5/1981 |
| WO | 2012039835 A1 | 3/2012 |
| WO | 2012071048 A1 | 5/2012 |
| WO | 2014182767 A1 | 11/2014 |

OTHER PUBLICATIONS

International Search Report from PCT Application No. PCT/US2018/055797, dated Feb. 5, 2019.
International Search Report from PCT Application No. PCT/US2016/048532, dated Oct. 26, 2016.
Ossur, "Icecross Seal-In X5: For TT/TF Users, Instructions for Use", www.ossur.com, 2010, 68 Pages.
"Prototype Prosthetic Cooling System Wins UTSA Entrepreneurship Competition", OandP.com, May 3, 2013, 3 Pages Retrieved

(56) References Cited

OTHER PUBLICATIONS from Internet on Apr. 20, 2016, http://www.oandp.com/articles/news_2013-05-03_02.asp.

* cited by examiner

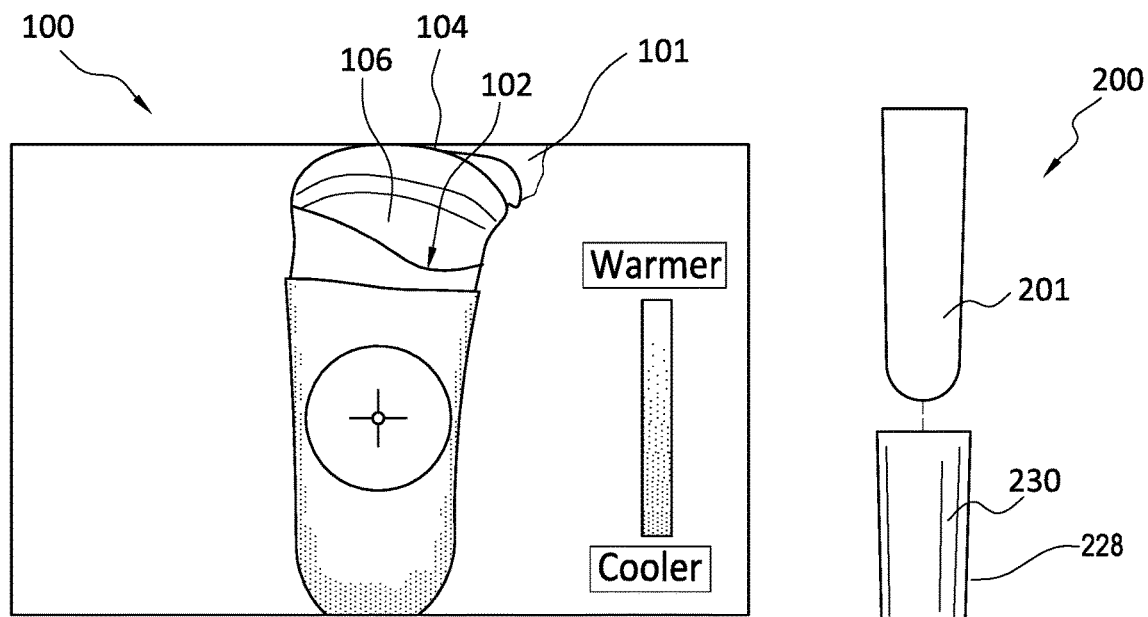
FIG. 2
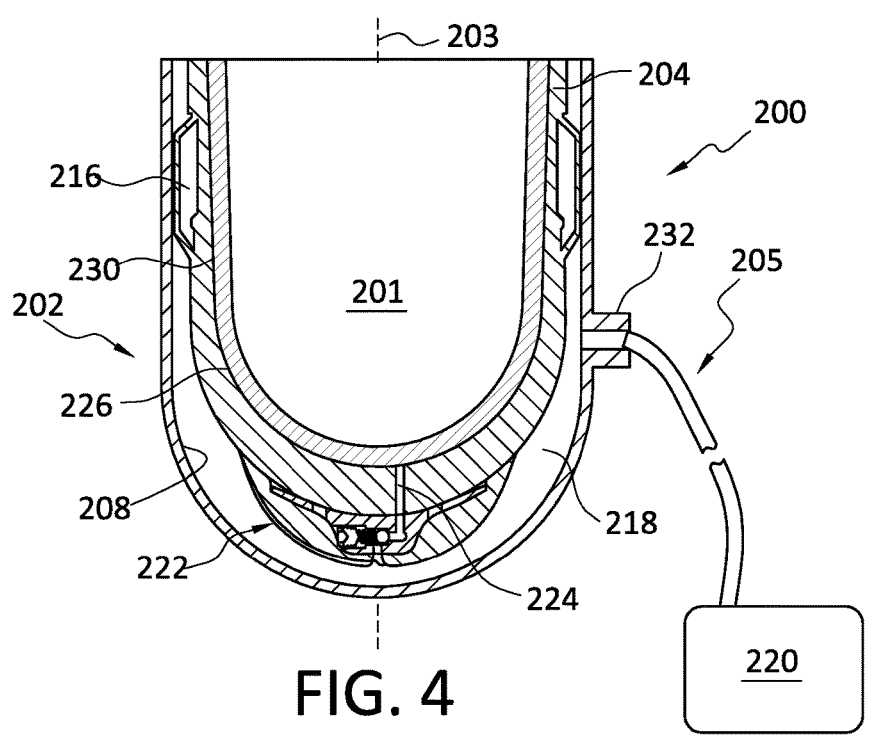
FIG. 3
FIG. 4

HEAT AND SWEAT MANAGEMENT SYSTEM

TECHNICAL FIELD

The disclosure relates to heat and sweat management systems for a prosthetic system.

BACKGROUND

Prosthetic liners made of solid elastomers like silicone, copolymer gel, or polyurethane have been commercially available and used for a number of years as the media next to the skin in the majority of lower extremity prostheses.

Such liners have solved many issues like friction and pressure distribution; however, it has been difficult to achieve effective heat and sweat management when using a non-porous interface. For instance, moisture (e.g. sweat or condensation) within the liner can adversely affect limb health. Moisture decreases the friction suspending the liner on the residual limb. This can cause a pistoning action, which describes the relative movement between the liner and the residual limb. Excessive limb pistoning tends to lead to friction-related injuries such as friction blisters and skin irritation. It also creates the potential for catastrophic failure of the suspension of the limb. Problems such as dermatitis and infection are also common, particularly if the liner and residual limb are not cleaned appropriately or frequently.

Attempts have been made to remove heat and sweat using different liner type suction interfaces. Disadvantageously, such interfaces are relatively complex, short lasting, ineffective, uncomfortable, and inevitably prohibit their use with a large majority of users. Such liner-suction interfaces may additionally present adverse health risks. Vacuums may be useful for withdrawing fluids as well as heat, such as from the inside of a prosthetic liner, but significant drawbacks to existing liner-suction interfaces prevent the safe, effective, and simple use of vacuums for heat and sweat removal in prosthetic systems.

Chief among these drawbacks are the problems created by applying too great of a magnitude or intensity of a vacuum to a user's skin. It has been found that elevated vacuum being applied directly to the skin surface for sweat removal or other purposes can be very risky and subject to create blisters and problems if the vacuum level is beyond or below about 50 mmHg below atmospheric pressure. Elevated vacuum for suspension applied to the outside of the prosthetic liner to secure the liner to a prosthetic socket is commonly 250 mmHg or more, which is far beyond what has been found to be comfortable or desirable as a vacuum level inside the prosthetic liner.

Thus existing devices must navigate a tension between configuring a level or intensity of vacuum that is applied to a user that effectively suspends the residual limb within the socket but is dangerous and uncomfortable against a user's skin in order to effectively remove heat and sweat, or alternatively the level or intensity of vacuum that is applied to a user is maintained at a lower level that provides ineffective suspension of the residual limb within the socket (and attendant risks such as risk of catastrophic failure, reduced proprioception, discomfort, and others) but reduces the health risks associated with elevated vacuums.

Accordingly, there is a need for a prosthetic system with an improved liner-suction interface that allows for effective suspension of a residual limb within a socket and removes heat and sweat with reduced risk of adverse health effects.

SUMMARY

Embodiments of the present disclosure include a prosthetic liner, and a valve assembly arranged for regulating fluid communication between an interface region defined between the prosthetic liner and a residual limb positioned in the prosthetic liner, and a suspension chamber defined between the prosthetic liner and a prosthetic socket.

The valve assembly is configured such that a vacuum in the suspension chamber selectively moves the valve assembly between a closed position in which the valve assembly fluidly separates the suspension chamber from the interface region, and an open position in which a portion of the vacuum in the suspension chamber draws fluid from the interface region via the valve assembly into the suspension chamber. The portion of vacuum directed to the interface region by the valve assembly can provide a comfortable level of suction inside of the prosthetic liner for sweat and heat removal, reducing the likelihood of problems that can result when too much vacuum is applied directly to a skin surface. The remaining vacuum in the suspension chamber provides reliable prosthetic suspension. The prosthetic system thus offers an improved liner-suction interface that allows for effective suspension of a residual limb within a socket and removes heat and sweat with reduced risk of adverse health effects. Furthermore, because the vacuum in the suspension chamber actuate the valve assembly, the prosthetic system allows for both prosthetic suspension and heat and moisture removal from inside the prosthetic liner to be accomplished using a single pump mechanism or vacuum source, substantially decreasing the complexity and expense of the prosthetic system.

According to a variation, when the vacuum in the suspension chamber exceeds an actuating vacuum comprising a specific pressure differential across the valve assembly or between the suspension chamber and the interface region, the valve assembly automatically moves to the open position, pulling fluid from the interface region into the suspension chamber and out of the prosthetic system through a pump mechanism. As fluids move into the suspension chamber, the valve assembly can return to the closed position when the pressure differential across the valve assembly decreases below the actuating vacuum, thereby resealing the suspension chamber.

This automatic opening and closure of the valve assembly with the actuating vacuum advantageously helps ensure that adequate suction is present in the suspension chamber so that the prosthetic socket does not fall off the residual limb, while allowing the released vacuum from the suspension chamber to pull fluid from the interface region as soon as the prosthetic system is capable of doing so. Further, by controlling the pressure differential between the suspension chamber and the interface region, the valve assembly helps eliminate or prevent problems associated with too much vacuum being applied directly to the skin surface of the residual limb.

BRIEF DESCRIPTION OF THE DRAWINGS

These and other features, aspects, and advantages of the present disclosure will become better understood regarding the following description, appended claims, and accompanying drawings.

FIG. 2 shows a schematic thermal image of the prosthetic system of FIG. 1.

FIG. 3 shows a sectional view of a prosthetic system according to another embodiment.

FIG. 4 shows a partial sectional view of the distal portion of the prosthetic system of FIG. 3.

DETAILED DESCRIPTION OF VARIOUS EMBODIMENTS

Figure 1:
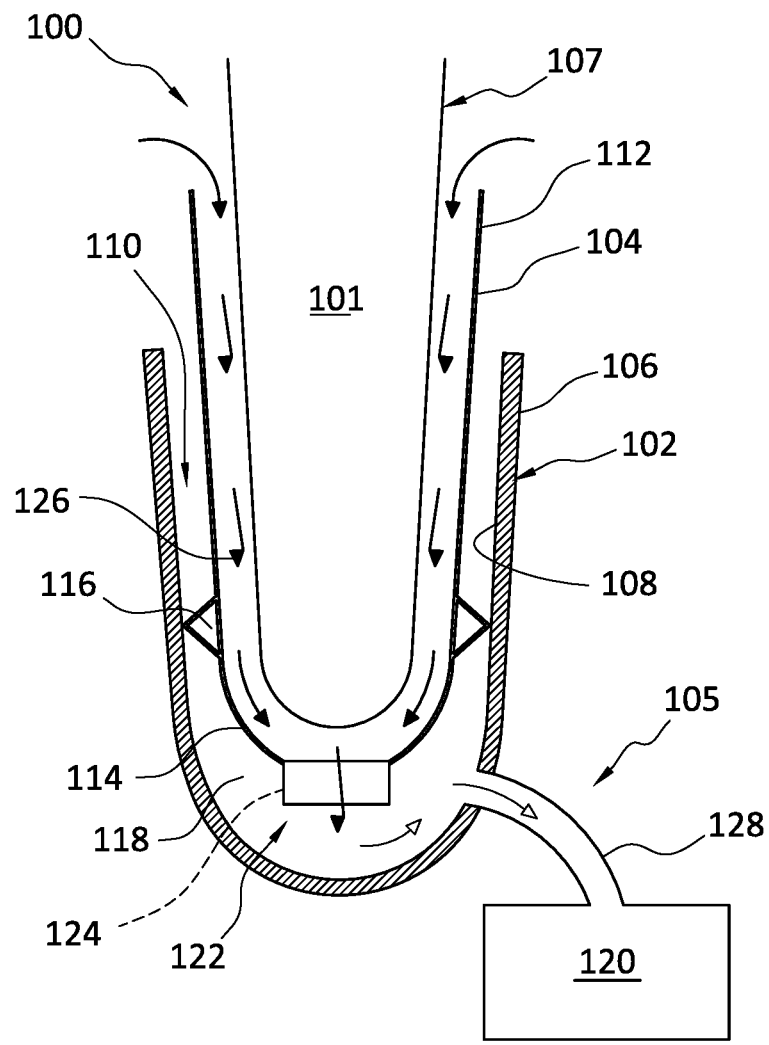
FIG. 1 shows a schematic view of a prosthetic system according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

For further ease of understanding the embodiments as disclosed herein, a description of a few terms is necessary. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the prosthetic system embodiments. The term "rigid" is intended to denote that an element of the system is generally devoid of flexibility. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of elements that provide support and are free-standing; however, such elements may have some degree of flexibility or resiliency.

It will be understood that unless a term is expressly defined in this application to possess a described meaning, there is no intent to limit the meaning of such term, either expressly or indirectly, beyond its plain or ordinary meaning. Any element in a claim that does not explicitly state "means for" performing a specified function, or "step for" performing a specific function is not to be interpreted as a "means" or "step" clause as specified in 35 U.S.C. § 112(f).

FIG. 1 illustrates a prosthetic system 100 according to an embodiment including a prosthetic socket 102, a prosthetic liner 104, and a heat management system 105. The prosthetic socket 102 has an outer surface 106 and an opposing inner surface 108 defining a socket cavity 110. The inner surface 108 can include a closed-ended cup with an open proximal end and closed distal end. The open proximal end of the inner surface 108 is adapted to receive a distal portion of the residual limb 101 to be located in the socket cavity 110.

The prosthetic liner 104 is adapted to receive the residual limb 101 therein and to provide an interface between the residual limb 101 and the prosthetic socket 102. The prosthetic liner 104 includes a body 107 that extends between a proximal end 112 and a distal end 114 and can comprise an air-impermeable elastomeric material such as silicone, copolymer gel, polyurethane, urethane, thermoplastic elastomer, RTV rubber, combinations thereof, or any other appropriate material. The prosthetic liner 104 is typically donned on the residual limb 101 and the residual limb 101 and the prosthetic liner 104 are then inserted in the socket cavity 110 of the prosthetic socket 102. The softer elastomer of the prosthetic liner 104 adheres to the skin of the residual limb 101 frictionally to thereby secure the residual limb 101 within the prosthetic liner 104. The prosthetic liner 104, on the other hand, remains contained within the socket cavity 110 after it has been fully inserted into the distal end area of the socket cavity 110 by creating a seal between the prosthetic socket 102 and the prosthetic liner 104.

As used herein, a "seal" may refer to a feature or component of the prosthetic system 100 that allows a vacuum or hypobaric pressure to be formed between the prosthetic liner 104 and the prosthetic socket 102. In the illustrated embodiment, a seal element 116 is associated with or defined by the prosthetic liner 104 to help maintain a vacuum between the prosthetic socket 102 and the prosthetic liner 104 by preventing atmospheric pressure from entering a space defined between the prosthetic liner 104 and the prosthetic socket 102.

Pulling forces applied to the prosthetic liner 104 will result in a suction being created between the prosthetic liner 104 and the prosthetic socket 102. Referring to FIG. 1, a suspension chamber 118 is defined distally of the seal element 116 and between at least a portion of the outer surface 109 of the prosthetic liner 104 and a corresponding portion of the inner surface 108 of the prosthetic socket 102, substantially isolating this area from atmospheric pressure.

If desired, a hypobaric pressure or vacuum can be created in the suspension chamber 118 by attaching a pump mechanism 120 or other device that enables evacuation of atmosphere and/or fluid in the suspension chamber 118. The pump mechanism 120 can be attached to the suspension chamber 118 in any suitable manner but is shown fluidly connected to the suspension chamber 118 via a tube 128. Creating the hypobaric pressure or vacuum in the suspension chamber 118 creates suction which helps reduce the likelihood of the residual limb 101 undesirably moving with the prosthetic socket 102 and/or potentially separating from the prosthetic system 100 altogether.

The pump mechanism 120 can be placed at any position and is not restricted to a particular location. The pump mechanism 120 can be located on the foot, at the knee, on the socket, or at any other suitable location. In addition, the pump mechanism 120 can include any suitable type of pump mechanism. For instance, the pump mechanism 120 may be a mechanical pump as described in U.S. Pat. Nos. 9,615,946, 9,486,335, 9,044,348, and 9,072,617 incorporated by reference and belonging to the assignee of this disclosure. For example, a piston-type pump, a membrane-type pump, or a bladder-type pump may be used in the embodiments. An electronic pump may be used in place of a mechanical pump.

As described in more detail below, the heat management system 105 comprising a valve assembly 122 is adapted to controllably separate the vacuum for prosthetic suspension created in the suspension chamber 118 from inside of the prosthetic liner 104 and diverts a part of that vacuum to the inside of the prosthetic liner 104 to draw or remove fluids and/or heat from the inside of the prosthetic liner 104. It will be appreciated that the term "fluid" may refer to any liquid or gas, including, but not limited to, water, sweat, air, vapor, or other suitable substance.

This controlled separation and diversion of the vacuum or hypobaric pressure in the suspension chamber 118 advantageously provides reliable prosthetic suspension and helps avoid problems that result when too much vacuum is applied directly to a skin surface. It has been found that hypobaric pressure or elevated vacuum applied directly to the skin surface of the residual limb 101 for sweat removal or other purposes can be risky and subject to create blisters and other problems if the vacuum level is beyond about 50 mmHg below atmospheric pressure. Elevated vacuum of hypobaric pressure for prosthetic suspension applied to the outside of a prosthetic liner to secure it to a prosthetic socket is commonly 250 mmHg or greater, which is well above what has been found to be comfortable or desirable as a vacuum level inside a prosthetic liner, especially for significant periods of use.

Referring to FIG. 1, an aperture 124 defined in the distal end 114 of the prosthetic liner 104 fluidly connects the suspension chamber 118 and an interface region 126 defined between the inner surface 111 of the prosthetic liner 104 and the residual limb 101. The valve assembly 122 is arranged for regulating fluid communication between the suspension chamber 118 and the interface region 126 via the aperture 124. The valve assembly 122 is shown situated in the aperture 124 but may be positioned in any suitable location in the prosthetic system 100.

In an embodiment, the valve assembly 122 is configured so that the vacuum or hypobaric pressure generated by the pump mechanism 120 in the suspension chamber 118 selectively moves the valve assembly 122 between a closed position and an open position. In the closed position, the valve assembly 122 prevents fluid flow through the aperture 124, fluidly separating the suspension chamber 118 and the interface region 126. This separation allows the vacuum and suction in the suspension chamber 118 to reliably hold or secure the residual limb 101 in the prosthetic socket 102 at vacuum levels which are well beyond what would be comfortable for the residual limb 101 inside of the prosthetic liner 104. The prosthetic system 100 may thus be effectively retained on a user's limb 101 without causing discomfort, non-compliant use, or serious health risks.

In the open position, the valve assembly 122 proportions or permits a portion of the vacuum in the suspension chamber 118 to draw fluid from the interface region 126 into the suspension chamber 118 via the valve assembly 122. This has the effect of providing a controlled suction in the interface region 126, which can effectively and comfortably remove sweat and/or heat from the interface region 126 without undesirably impacting the residual limb 101 or compromising prosthetic suspension, as the open position wherein a degree of vacuum is applied to the interface region 126 is applied temporarily and selectively.

An actuating vacuum, comprising a selected pressure differential across the valve assembly 122 or between the suspension chamber 118 and the interface region 126, can move the valve assembly 122 between the open and closed positions. When the vacuum in the suspension chamber 118 exceeds the actuating vacuum, the valve assembly 122 automatically moves to the open position, drawing fluid from the interface region 126 into the suspension chamber 118.

Optionally, the fluid drawn into the suspension chamber 118 via the valve assembly 122 can be expelled from the prosthetic system 100 through the pump mechanism 120. In an embodiment, fluid drawn through the interface region 126 can include air pulled over a proximal edge at the proximal end 112 of the prosthetic liner 104 or through at least one inlet defined in the prosthetic liner 104. The air movement through the interface region 126 between the residual limb 101 and the prosthetic liner 104 can help transfer or remove heat from the residual limb 101, which, in turn, can prevent excess sweat and increase overall user comfort. This effect can be observed by measuring the temperature inside the prosthetic liner 104 and on the outside of the prosthetic liner 104 when air is pulled through the interface region 126 by the pump mechanism 120 at different flow rates. For instance, FIG. 2 shows a band or seriatim of cooler temperatures at the interface 126 between the residual limb 101 and the prosthetic liner 104 when air is pulled through the interface region 126 according to an embodiment of the present disclosure.

In other embodiments, fluid drawn through the interface region 126 can be sufficient to evaporate sweat generated in the interface region 126 during ambulation so that the user's skin stays dry. In yet other embodiments, the fluid drawn from the interface region 126 into the suspension chamber 118 can include sweat in liquid form. This has the effect of reducing the overall amount of sweat inside the prosthetic liner 104. This increases comfort and compliant use while improving the frictional engagement between the residual limb 101 and the prosthetic system 100, which reduces the risk and complications of pistoning.

As the fluid is pulled into the suspension chamber 118 from the interface region 126, the valve assembly 122 can automatically return to the closed position when the pressure differential across the valve assembly 122 decreases below the actuating vacuum. This advantageously helps ensure that adequate vacuum or suction is maintained in the suspension chamber 118 so that the prosthetic socket 102 does not fall off the residual limb 101. This also can help limit undesirable pistoning of the residual limb 101 within the prosthetic socket 102. Further, by controlling the pressure differential between the suspension chamber 118 and the interface region 126, the valve assembly 122 eliminates or limits problems associated with too much vacuum being applied directly to the skin surface of the residual limb 101.

The heat management system 105 thus allows a single pump mechanism or vacuum source to both promote comfortable movement of fluid and/or heat out of the prosthetic liner 104 and to maintain safe and secure prosthetic suspension between the prosthetic socket 102 and the residual limb 101.

According to a variation, the valve assembly 122 has a low-profile design integrated into the distal end 114 of the prosthetic liner 104. For instance, the socket cavity 110 of the prosthetic socket 102 does not have to be reshaped to accommodate the valve assembly 122. This beneficially allows the heat management system 105 to be integrated or used with existing or conventional sockets without structural modification. For instance, the valve assembly 122 can be integrated with the prosthetic liner 104 and enclosed within the cavity of a conventional or off-the-shelf prosthetic socket 102 without having to modify the prosthetic socket 102. In addition, the valve assembly 122 can be adapted to fit a number of different liners and sockets, providing versatility. The valve assembly 122 can be a one-way valve that only allows fluid to pass from the interface region 126 into the suspension chamber 118.

The actuating vacuum of the valve assembly 122 can be selected, set, or adjusted as desired. In an embodiment, the actuating vacuum of the valve assembly 122 can be set at or above vacuum levels typical for safe and effective prosthetic suspension to ensure that sufficient vacuum is maintained in the suspension chamber 118 during use of the prosthetic system 100. For instance, the actuating vacuum of the valve assembly 122 can be between about 250 mmHg and about 600 mmHg (e.g., about 375 mmHg), between about 280 mmHg and about 500 mmHg, between about 300 mmHg and about 400 mmHg, between about 320 mmHg and about 380 mmHg, or between about 340 mmHg and about 360 mmHg. In other embodiments, the actuating vacuum of the valve assembly 122 can be greater than about 250 mmHg, about 300 mmHg, about 350 mmHg, or about 400 mmHg. In other embodiments, the opening pressure of the valve assembly 122 can be higher or lower.

In other embodiments, the actuating vacuum of the valve assembly 122 can comprise a pressure differential where the magnitude of the vacuum in the suspension chamber 118 is greater than about 4, about 5, about 6 times, about 7 times, about 8 times, about 9 times, or about 10 times the magnitude of a vacuum in the interface region 126. In other embodiments, the actuating vacuum can comprise the vacuum in the suspension chamber 118 being greater than about 350 mmHg below atmospheric pressure in the interface region 126. Optionally, the actuating vacuum can be adjustable to control the amount of vacuum released to or pulled in the interface region 126 based on user activity level, weight, and/or other factors, advantageously providing the heat management system 105 greater control and versatility. For example, certain activities may lead to greater heat and sweat buildup in the interface region 126, necessitating more frequent removal; other activities may engender significantly less heat and sweat buildup, necessitating less frequent removal. Additionally, specific users may have different tolerances for elevated vacuum and/or sweat buildup.

According to a variation, the heat management system 105 is arranged to operate based on a user's gait, such as in a mechanical pump arrangement. For instance, as the user puts its weight on the prosthetic liner 104 and/or a prosthetic foot, such as upon heel strike, mid-stance, and/or toe-off, the user's weight can cause the pump mechanism 120 to compress. After the weight is removed, and/or shifted, the pump mechanism 120 can return toward its original configuration, drawing a vacuum inside the suspension chamber 118.

When the vacuum generated by the pump mechanism 120 in the suspension chamber 118 exceeds the actuating vacuum of the valve assembly 122, the valve assembly 122 can move automatically to the open position, allowing a portion of the vacuum in the suspension chamber 118 to draw fluid from the interface region 126 into the suspension chamber 118 via the valve assembly 122. This can create a controlled suction in the interface region 126, which can effectively remove fluid (e.g., sweat) and/or heat from the interface region 126 to the suspension chamber 118 and out through the pump mechanism 120. When the vacuum in the suspension chamber 118 drops below the actuating vacuum of the valve assembly 122, the valve assembly 122 can move automatically to the closed position, resealing the suspension chamber 118. This advantageously helps ensure that sufficient vacuum or suction is maintained above at least a baseline level of pressure in the suspension chamber 118 so that the prosthetic socket 102 does not fall off the residual limb 101.

Because the heat management system 105 can operate on motion of the user, it can remove more fluid (e.g., sweat) and/or heat when the user is participating in a higher activity event such as running, skiing, or hiking, increasing the efficiency of the heat management system 105. Further, because the heat management system 105 includes fewer moving parts and uses the vacuum in the suspension chamber 120 for both suspension and heat/sweat removal, the prosthetic system 100 is simpler than prior art systems, reducing the likelihood of the prosthetic system 100 malfunctioning or failing, and reducing the cost and complexity of the prosthetic system 100.

FIGS. 3-7 illustrate a prosthetic system 200 according to another embodiment of the present disclosure. Referring to FIGS. 3 and 4, the prosthetic system 200 can be similar to the previous embodiment shown in FIGS. 1 and 2, including a prosthetic socket 202, a prosthetic liner 204, and a heat management system 205 comprising a valve assembly 222. A seal element 216 is associated with the prosthetic liner 204 and a suspension chamber 218 is defined distally of the seal element 216 and between at least a portion of the outer surface 206 of the prosthetic liner 204 and a corresponding portion of the inner surface 208 of the prosthetic socket 202, substantially isolating this suspension chamber 218 from atmosphere. An interface region 226 is defined between an inner surface 207 of the liner 204 and an outer surface of the residual limb 201.

The heat management system 205 may include a pump mechanism 220 fluidly connected to the suspension chamber 218, an aperture 224 in the distal end of the liner 204 and in fluid communication with the suspension chamber 218 and the interface region 226, and the valve assembly 222 arranged to provide controlled fluid communication between the suspension chamber 218 and the interface region 226 via the aperture 224.

The pump mechanism 220 is fluidly connected to the suspension chamber 218 via a port 232 defined in the sidewall of the socket 202. Similar to other embodiments, the valve assembly 222 is arranged so that the vacuum generated by the pump mechanism 220 in the suspension chamber 218 selectively and automatically moves the valve assembly 222 between a closed position and an open position.

In the closed position, the valve assembly 222 prevents fluid flow through the aperture 224 to fluidly separate the suspension chamber 218 and the interface region 226. This separation allows the elevated vacuum in the suspension chamber 218 to reliably hold or secure the residual limb 201 in the prosthetic socket 202 at vacuum levels which are well beyond what would be comfortable if applied directly to the residual limb 201 inside of the prosthetic liner 204.

In the open position, the valve assembly 222 proportions or permits a portion of the vacuum in the suspension chamber 218 to draw fluid through and/or from the interface region 226 into the suspension chamber 218 via the valve assembly 222. This has the effect of providing a controlled suction in the interface region, which can effectively and comfortably remove sweat and/or heat from the interface region 226 without undesirably impacting the residual limb 101 or compromising prosthetic suspension. Further, the functions of both prosthetic suspension and fluid removal from the inside of the prosthetic liner 204 are accomplished using a single pump mechanism 220, decreasing the cost and complexity of the prosthetic system 200 and increasing user comfort and compliant use.

Optionally, a flow structure 230 is positionable in the interface region 226. The flow structure 230 can help maintain the connection between the prosthetic liner 204 and the residual limb 201 while facilitating the flow of fluid through the interface region 226. For example, the flow structure 230 can define a plurality of flow channels through the interface region 226, helping to direct heat and sweat towards an aperture 224. The flow structure 230 can have a sock-like configuration including a generally continuous sidewall 228, an open top, and a closed bottom. In an embodiment, the flow structure 230 comprises a 3D knitted silicone sock donned on the inner surface of the liner 204.

Figure 5:
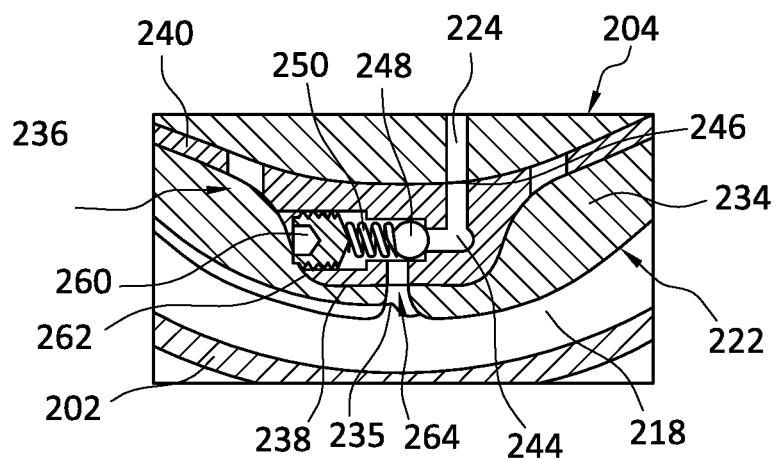
FIG. 5 shows a detailed sectional view of the distal portion of the prosthetic system of FIG. 3.
Figure 6:
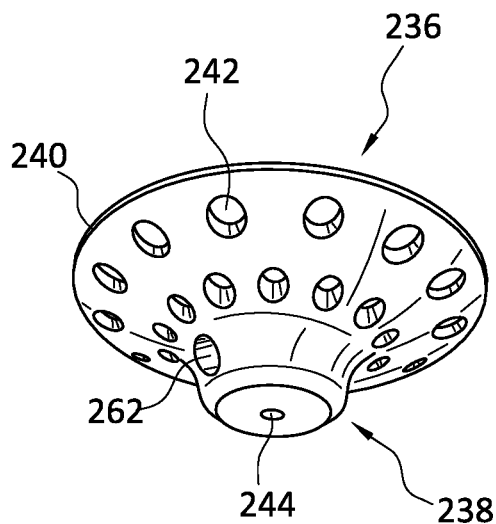
FIG. 6 shows a perspective view of the valve housing of a heat and sweat management system for a prosthetic system according to an embodiment.
Figure 7:
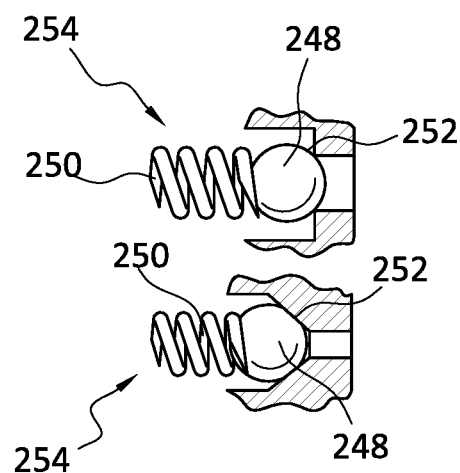
FIG. 7 shows a cross-sectional view of the valve according to an embodiment.

The valve assembly 222 will now be described in more detail in reference to FIGS. 5-7. According to a variation, the valve assembly 222 can be integrated into an umbrella 234 attached to the prosthetic liner 204. The umbrella 234 can be made of a rigid polymer and molded to the outer surface of the prosthetic liner 204. This advantageously conceals the valve assembly 222 and forms an airtight connection between the umbrella 234 and the prosthetic liner 204. A hole 235 is formed through the umbrella 234 so that fluid (e.g. air and sweat) can exit the valve assembly 222 through the umbrella 234. The hole 235 generally corresponds to an outlet of the valve housing 236 defined below.

As seen, the valve assembly 222 comprises a valve housing 236 carrying a valve unit 254 including a ball member 248 and a resilient element comprising a spring member 250. The valve housing 236 includes a main body 238 and a radial flange 240 extending circumferentially about the main body 238. The radial flange 240 is sized and configured to increase the connection area between the prosthetic liner 204, the umbrella 234 and the valve housing 236. Optionally, the radial flange 240 defines a plurality of through holes 242 to reduce weight and/or to help form a mechanical lock between the valve housing 236 and the umbrella 234, for example by way of the rigid polymer material of the umbrella 234 extending through and engaging the through holes 242. The valve housing 236 may be formed of aluminum or any suitable material.

The main body 238 may define a passageway 244 extending between first and second openings. The first opening can define an inlet 246 in fluid communication with the passageway 244 and the aperture 224. The second opening can define an outlet 264 in fluid communication with the suspension chamber 218 and the inlet 246 via the passageway 244.

The passageway 244 can include an enlarged portion that defines a seat 252 for the ball member 248. In the illustrated embodiment, the seat 252 comprises a planar or flat seat. This arrangement beneficially allows the valve assembly 222 to seal at lower pressures (e.g., vacuum pressures). However, it will be appreciated that the geometries of the seat 252 and the ball member 248 are exemplary only and other geometries are possible. For instance, the seat 252 can comprise a conical seat having a diameter that tapers away from the inlet 246 as also shown in FIG. 7. This arrangement beneficially helps the ball member 248 self-center in the seat 252.

In an embodiment, the valve unit 254 can be oriented in a transverse direction relative to a longitudinal axis 203 of the prosthetic system 200 or the prosthetic liner 204 within the passageway 244. This has the effect of reducing the overall height of the valve housing 236 on the distal end of the prosthetic liner 204. Such arrangement of the valve housing 236 beneficially allows the valve assembly 222 to be more easily integrated or used with existing or conventional sockets without substantial structural modifications. In addition, the valve assembly 222 can be adapted to fit a number of different liners and sockets, providing versatility.

The valve unit 254 is positioned in the passageway 244 such that the ball member 248 is located between the seat 252 and the spring member 250 and adapted to selectively engage and/or interact with the seat 252. Generally, when the ball member 248 engages or contacts the seat 252, the valve assembly 222 is in the closed position (shown in FIG. 5). In the closed position, the ball member 248 is forced against the seat 252 to prevent fluid flow through the aperture 224, which, in turn, fluidly separates the suspension chamber 218 and the interface region 226.

When the ball member 248 is disengaged from the seat 252, the valve assembly 222 is in an open position. In the open position, the aperture 224 is unsealed and fluid communication between the interface region 226 and the suspension chamber 218 is established, allowing a portion of the vacuum in the suspension chamber 218 to draw fluid through and/or from the interface region 226. This has the effect of creating a controlled suction at the aperture 224 and in the interface region 226, which can effectively and comfortably remove sweat and/or heat from the interface region 226 without compromising prosthetic suspension, as the controlled suction is not sustained for such periods of time as to create adverse health effects or discomfort against a user's skin.

The spring member 250 is adapted to bias the valve assembly 222 toward the closed position. For instance, in the closed position, the spring member 250 biases the ball member 248 toward the seat 252 of the main body 238, resealing the suspension chamber 218 and creating a fluid separation of the vacuum in the suction chamber 218 and the interface region 226. When the valve assembly 222 moves from the closed position toward the open position, the ball member 248 compresses or further compresses the spring member 250 between a retainer member 260 and the ball member 248 until it reaches an actuating vacuum. As the pressure differential across the valve assembly 222 drops below the actuating vacuum of the valve assembly 222, stored energy in the spring member 250 can force the ball member 248 back into the seat 252 to return the valve assembly 222 to the closed position. Thus, the spring member 250 can help automatically close the valve assembly 222 at a desired pressure.

The spring member 250 can comprise any suitable member. For example, the spring member 250 can comprise a compression spring. Further, while one spring member 250 is shown, in other embodiments, the valve unit 254 can include two, three, or any other number of spring members and ball members. The spring member 250 can be made from steel, alloys, plastic, or any other appropriate material. The spring member 250 and the ball member 248 may be custom designed or configured to create a desired actuation pressure, by taking into account the spring constant and spring length.

In use, the pump mechanism 220 generates a vacuum in the suspension chamber 218. When the vacuum in the suspension chamber 218 exceeds the actuating vacuum of the valve assembly 222 (i.e. the pressure in the suspension chamber 218 drops below the actuating vacuum threshold), the ball member 248 is forced off the seat 252 to move the valve assembly 222 to the open position, which, in turn, allows a portion of the vacuum in the suspension chamber to pull fluid from the interface region 226 into the suspension chamber 218 via the valve assembly 222.

As fluid is pulled into the suspension chamber 218 from the interface region 226, the vacuum in the suspension chamber 218 can decrease below the actuating vacuum (i.e. the pressure in the suspension chamber 218 increases above the actuating vacuum threshold), such that the valve assembly 222 automatically returns to the closed position due to the bias of the spring member 250, resealing the suspension chamber 218. This advantageously helps ensure that sufficient vacuum or suction is maintained in the suspension chamber 218 so that the prosthetic socket 202 does not fall off the residual limb 201. Further, by controlling the pressure differential between the suspension chamber 218 and the interface region 226, the valve assembly 222 eliminates or limits problems associated with too much vacuum applied directly to the skin surface of the residual limb 201.

According to a variation, the retainer member 260 can be threadedly attached to a hole 262 defined in the side of the main body 238 such that the position of the retainer member 260 relative to the ball member 248 can be adjusted by rotating the retainer member 260 within the hole 262, which, in turn, can influence the actuating vacuum of the valve assembly 222 by adjusting the force exerted on the ball member 248 by the spring member 250. The actuating vacuum thus can be adjusted by varying the position of the retainer member 260 relative to the ball member 248. The opening pressure adjustment can be made by the user or a clinician based on activity level or other factors. For instance, a lower opening pressure could be used for periods of high activity like running in which increased amounts of sweat and heat are generated, while a higher opening pressure setting could be used for periods of rest in which decreased amounts of sweat and heat are produced.

The configuration of the valve assembly 222 described herein is to be regarded as exemplary only, as any suitable configuration of the valve assembly is possible. For example, the valve assembly can be a check valve, a swing-check valve, a luer check valve, a miniature check valve, or any other suitable valve.

Figure 8:
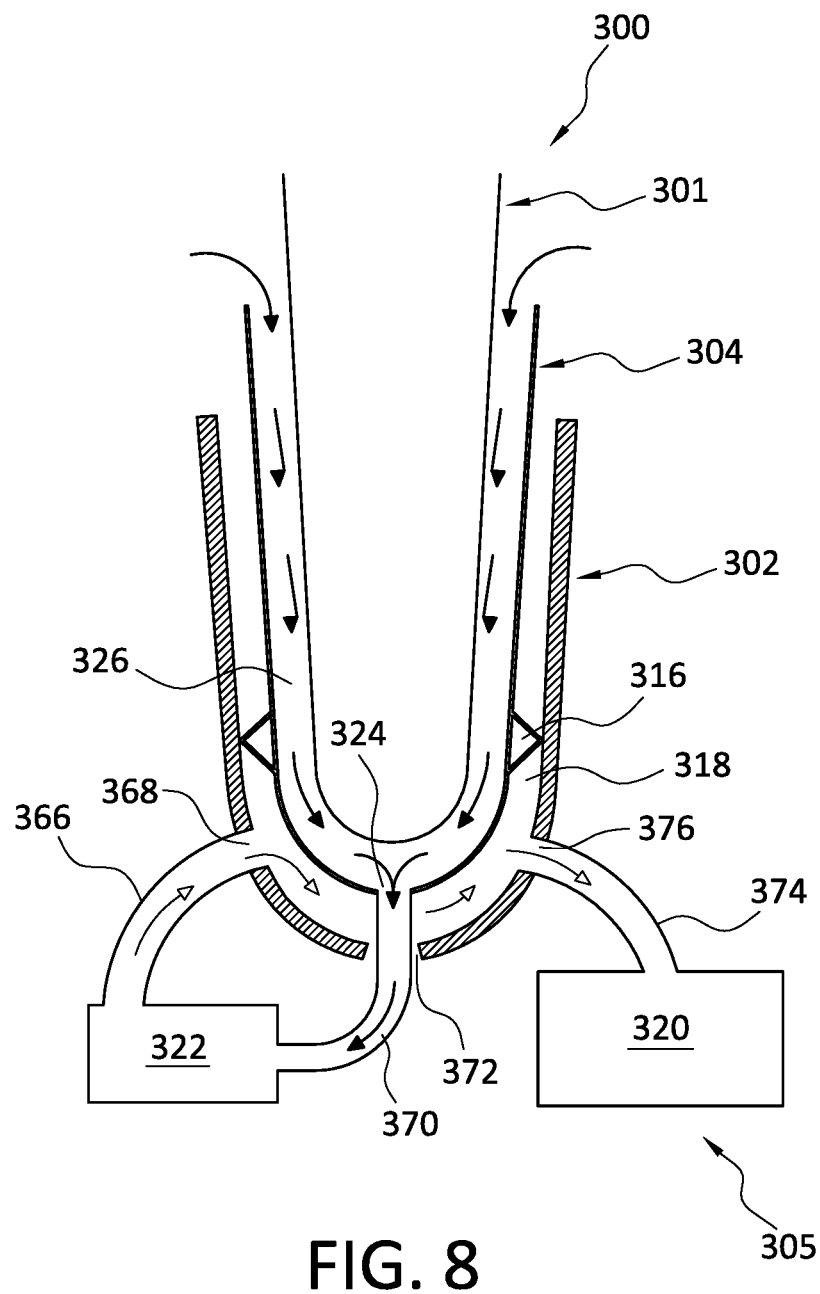
FIG. 8 shows a schematic view of a prosthetic system according to another embodiment.

FIG. 8 illustrates a prosthetic system 300 according to yet another embodiment. The prosthetic system 300 can be similar to the previous embodiments and may include a prosthetic socket 302, a prosthetic liner 304, and a heat management system 305 comprising a valve assembly 322. A seal element 316 is associated with the prosthetic liner 304 and a suspension chamber 318 is defined distally of the seal element 316 and between at least a portion the outer surface of the prosthetic liner 304 and a corresponding portion of the inner surface of the prosthetic socket 302, substantially isolating this area from atmosphere. An interface region 326 is defined between an inner surface of the prosthetic liner 304 and an outer surface of the residual limb 301.

The heat management system 305 can include a pump mechanism 320 fluidly connected to the suspension chamber 318, an aperture 324 in the distal end of the prosthetic liner 304 and fluidly connecting the suspension chamber 318 and the interface region 326, and the valve assembly 322 arranged to control fluid flow through the aperture 324.

Similar to other embodiments, the valve assembly 322 is arranged so that the vacuum generated by the pump mechanism 320 in the suspension chamber 318 selectively moves the valve assembly 322 between a closed position and an open position. In the closed position, the valve assembly 322 prevents fluid flow through the aperture 324 to fluidly separate the suspension chamber 318 and the interface region 326. This separation allows the vacuum and suction in the suspension chamber 318 to reliably hold or secure the residual limb 301 in the prosthetic socket 302 at vacuum levels which are well beyond what would be comfortable for the residual limb 301 inside of the prosthetic liner 304, while protecting the residual limb from harmful and prolonged exposure to the elevated vacuum.

In the open position, the valve assembly 322 proportions or permits a portion of the vacuum in the suspension chamber 318 to draw fluid from the interface region 326 into the suspension chamber 318. This has the effect of providing a controlled suction in the interface region, which can effectively and comfortably remove sweat and/or heat from the interface region 326 without compromising prosthetic suspension by decreasing the suction level. Further, both prosthetic suspension and effective fluid removal from the inside of the prosthetic liner 304 are accomplished using a single pump mechanism 320, decreasing the cost and complexity of the prosthetic system 300 and increasing user comfort.

As seen, the valve assembly 322 is positioned outside of the prosthetic socket 302 and a first tube 366 extends between the valve assembly 322 and a first opening 368 defined in the prosthetic socket 302. The first opening 368 is in fluid communication with suspension chamber 318. A second tube 370 is connected to the aperture 324 so as to be in fluid communication with the interface region 326 and extends through a second opening 372 in the distal end of the socket 302 to the valve assembly 322. A third tube 374 extends between the pump assembly 320 and a third opening 376 in the socket 302 that is in fluid communication with the suspension chamber 318.

In use, the pump mechanism 320 generates a vacuum in the suspension chamber 318. When the vacuum in the suspension chamber 318 exceeds the actuating vacuum of the valve assembly 322, the valve assembly 322 moves to the open position, which, in turn, permits a portion of the vacuum in the suspension chamber 318 to pull fluid from the interface region 326 via the second tube 370, to the suspension chamber 318 via the first tube 366 and then out through the pump mechanism 320 via the third tube 374.

Because the valve assembly 322 is positioned outside of the prosthetic socket 302, the valve assembly 322 can be used with existing or conventional sockets without substantial modifications. For instance, the socket cavity of the prosthetic socket 302 does not have to be reshaped, but rather openings 368, 372, 376 would simply have to be formed in the prosthetic socket 302 to install the heat management system 305. The pump mechanism 320 can be placed at any position and is not restricted to a particular location.

As fluid is pulled into the suspension chamber 318 from the interface region 326, the vacuum in the suspension chamber 318 can decrease below the actuating vacuum such that the valve assembly 322 automatically returns to the closed position, resealing the suspension chamber 318 and reestablishing a fluid separation between the suspension chamber 318 and the interface region 326. The heat management system 305 can thus use the vacuum generated in the suspension chamber 318 by the pump mechanism 320 to both promote the movement of fluid through the interface region 326 and help maintain safe and secure suspension. As with other embodiments, the movement of fluid through the interface region 326 can advantageously lower the temperature of the residual limb 301 and/or remove sweat from the interface region 326. These benefits may be achieved with minimal cost, complications, and user effort as the heat management system 305 is easily added to a socket/liner prosthetic system 300.

Figure 9:
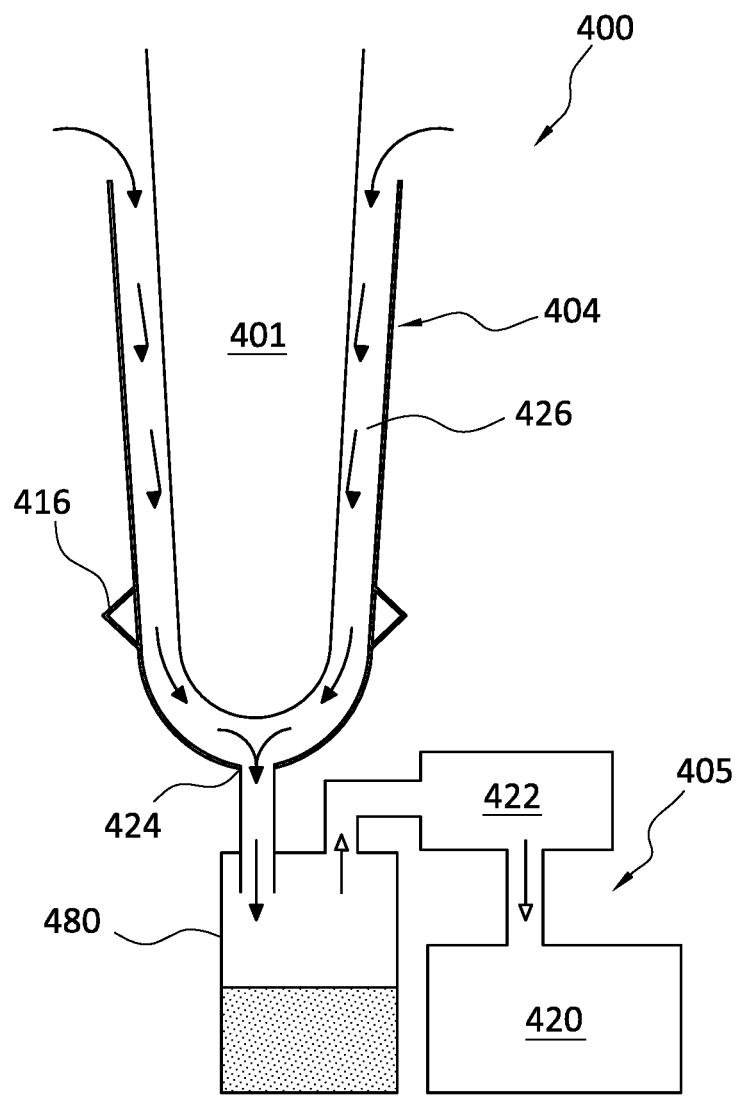
FIG. 9 shows a schematic view of a prosthetic system according to another embodiment.

FIG. 9 illustrates a prosthetic system 400 according to yet another embodiment. The prosthetic system 400 includes a liner 404 and a heat management system 405 comprising a valve assembly 422. A seal element 416 is associated with the liner 404 and an interface region 426 is defined between an inner surface of the liner 404 and an outer surface of the residual limb 401. A pump mechanism 420 is fluidly connected to the interface region 426.

The heat management system 405 can include an aperture 424 in the distal end of the prosthetic liner 404 and in fluid communication with the interface region 426, and the valve assembly 422 arranged to control flow between the interface region 426 and the pump mechanism 420. The valve assembly 422 is arranged so that the vacuum generated by the pump mechanism 420 selectively moves the valve assembly 422 between a closed position and an open position. A reservoir 480 is arranged to collect liquid or sweat being pulled out of the interface region 426.

In use, the pump mechanism 420 generates a vacuum in the heat management system 405. When the vacuum in the heat management system 405 exceeds an actuating vacuum of the valve assembly 422, the valve assembly 422 moves to the open position, allowing a portion of the vacuum to draw fluid from interface region 426 to the reservoir 480. In an embodiment, fluid delivered to the reservoir 480 can be collected in the reservoir 480. The reservoir 480 can be removable from the heat management system 405 and/or disposable. This beneficially allows liquids such as sweat to be measured and/or collected in the reservoir 480 and then disposed of. Furthermore, the pump mechanism 420 does not have to be capable of moving liquids because the removed liquids fall out into the reservoir 480 before reaching the pump mechanism 420.

As the vacuum from the pump mechanism 420 decreases below the actuating vacuum of the valve assembly 422, the valve assembly 422 automatically returns to the closed position, inhibiting fluid flow between the interface region 426 and the pump mechanism 420. Optionally, fluid collected in the reservoir 480 can be drawn from the reservoir 480 through the valve assembly 422 and the pump mechanism 420.

Embodiments of the present disclosure can thus advantageously allow for reliable prosthetic suspension and comfortable vacuum levels inside of the prosthetic liner for sweat and heat removal. Furthermore, both prosthetic suspension and fluid removal from inside the prosthetic liner can be accomplished using a single pump mechanism or vacuum source, substantially decreasing the complexity and expense of the prosthetic system.

The various aspects and embodiments disclosed herein are for purposes of illustration and are not intended to be limiting. For instance, the sealing element can be associated with the socket or omitted from the prosthetic system. In other embodiments, the prosthetic system can include two or more pump mechanisms and/or valve assemblies. In other embodiments, the valve assembly can be integrated into the liner body of the liner. For instance, examples of suitable valve assembly arrangements can be found in U.S. Pat. No. 8,679,194, owned by the assignee of this disclosure and incorporated herein. Moreover, the flow structure can be included with any of the embodiments described herein.

Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A prosthetic system comprising:
a prosthetic liner adapted to provide an interface between a residual limb and a prosthetic socket; and
a valve assembly arranged for regulating fluid communication between an interface region defined between the prosthetic liner and the residual limb and a suspension chamber defined between the prosthetic liner and the prosthetic socket, wherein a vacuum in the suspension chamber selectively moves the valve assembly between a closed position in which the valve assembly fluidly separates the suspension chamber from the interface region, and an open position in which a portion of the vacuum in the suspension chamber draws fluid from the interface region via the valve assembly into the suspension chamber, wherein the valve assembly is arranged to limit the vacuum level between the liner and residual limb to about 50 mmHg;
wherein the prosthetic liner includes a seal element extending circumferentially from a distal end portion of the prosthetic liner and the seal element protrudes from the prosthetic liner to seal against an inner surface of the prosthetic socket, the suspension chamber being defined distally of the seal element;
wherein the valve assembly is arranged to move to the open position when the vacuum in the suspension chamber exceeds an actuating vacuum comprising a pressure differential between the suspension chamber and the interface region;
wherein the actuating vacuum is greater than about 250 mmHg;
wherein the valve assembly is a one-way valve arranged to only allow fluid to pass from the interface region into the suspension chamber through said one-way valve, and is located at a distal end of the distal end portion of the prosthetic liner;
wherein the valve assembly is integrated in the distal end of the distal end portion of the prosthetic liner;
wherein the valve assembly fluidly communicates with an aperture defined by the distal end of the prosthetic liner, the aperture connects the suspension chamber and the interface region;
wherein the valve assembly comprises a valve housing carrying a valve unit oriented in a transverse, horizontal direction relative to a vertical direction along which a longitudinal axis of the prosthetic liner is oriented.

2. The prosthetic system of claim 1, wherein the valve assembly moves to the closed position when the vacuum in the suspension chamber decreases below the actuating vacuum.

3. The prosthetic system of claim 1, wherein the valve housing has a main body defining a passageway extending between an inlet connected to the aperture, and an outlet connected to the suspension chamber.

4. The prosthetic system of claim 3, wherein the valve housing includes a radial flange extending circumferentially about the main body.

5. The prosthetic system of claim 1, wherein the valve unit comprises a spring member and a ball member biased by the spring member and arranged to selectively seal against a seat defined by the valve housing.

6. The prosthetic system of claim 5, wherein the ball member is arranged to translate in the transverse, horizontal direction within the valve housing.

7. The prosthetic system of claim 5, wherein the actuating vacuum is adjustable by varying a position of the ball member relative to a retainer member threadedly attached to the valve housing.

* * * * *